US012674446B2

(12) United States Patent (10) Patent No.: US 12,674,446 B2
Khan et al. (45) Date of Patent: Jul. 7, 2026

---

(54) REUSABLE FLUID PUMPING DEVICE

(71) Applicant: CareFusion 303, Inc., San Diego, CA (US)

(72) Inventors: Mohammed Mehtab Khan, Whitefield Bangalore (IN); Karthik Mr, Bangalore (IN); Saushthav Shrivastava, Bengaluru (IN); Akshay Srikanth, Bengaluru (IN); Abhishek Krishnan, Bengaluru (IN)

(73) Assignee: CAREFUSION 303, INC., San Diego, CA (US)

( * ) Notice: Subject to any disclaimer, the term of this patent is extended or adjusted under 35 U.S.C. 154(b) by 228 days.

(21) Appl. No.: 17/951,786

(22) Filed: Sep. 23, 2022

(65) Prior Publication Data

US 2024/0100246 A1 Mar. 28, 2024

(51) Int. Cl.
  *F04B 43/02* (2006.01)
  *A61M 5/142* (2006.01)
  (Continued)

(52) U.S. Cl.
  CPC ......... *F04B 43/02* (2013.01); *A61M 5/14224* (2013.01); *F04B 9/02* (2013.01);
  (Continued)

(58) Field of Classification Search
  CPC .. F04B 43/02; F04B 9/02; F04B 9/042; F04B 9/14; A61M 5/1413; A61M 2005/14506;
  (Continued)

(56) References Cited

U.S. PATENT DOCUMENTS 6,500,156 B1 12/2002 Stansbury
8,337,466 B2 12/2012 Salgia et al.
(Continued)

FOREIGN PATENT DOCUMENTS

DE 202006020237 U1 2/2008
EP 0478499 A1 4/1992
EP 2917582 B1 4/2018

OTHER PUBLICATIONS

International Search Report and Written Opinion for Application No. PCT/US2023/031534, dated Jan. 23, 2024, 19 pages.
(Continued)

*Primary Examiner* — Charles G Freay
(74) *Attorney, Agent, or Firm* — MASCHOFF BRENNAN

(57) ABSTRACT

Pump assemblies for use with an IV set are described herein. A pump assembly includes a rotatable crank, a piston rod, and a diaphragm assembly. The crank includes a crank profile defining a plurality of lobes. The piston rod includes a first follower and a second follower spaced apart from the first follower. The rotation of the crank relative to the piston rod causes the piston rod to reciprocate relative to the crank. The diaphragm assembly includes a housing and a diaphragm member. The diaphragm member is coupled to the housing and cooperatively defines a volume in fluid communication with the IV set. The diaphragm member is movable between an extended position configured to draw in fluid from the IV set and a contracted position configured to expel fluid into the IV set. The diaphragm member is coupled to the piston rod to reciprocate the diaphragm member.

14 Claims, 5 Drawing Sheets

(51) Int. Cl.

| | |
|---|---|
| *A61M 5/145* | (2006.01) |
| *F04B 9/02* | (2006.01) |
| *F04B 9/04* | (2006.01) |
| *F04B 9/14* | (2006.01) |
| *A61M 5/14* | (2006.01) |

(52) U.S. Cl.
CPC ................ *F04B 9/042* (2013.01); *F04B 9/14* (2013.01); *A61M 5/1413* (2013.01); *A61M 2005/14506* (2013.01); *A61M 5/14586* (2013.01)

(58) Field of Classification Search
CPC ......... A61M 2005/14269; A61M 2005/14586; A61M 5/14224

See application file for complete search history.

(56) References Cited

U.S. PATENT DOCUMENTS

| | | | | |
|---|---|---|---|---|
| 11,493,030 B2 * | 11/2022 | Singh | ...................... | F04B 43/02 |
| 2002/0057972 A1 * | 5/2002 | Barinaga | ................. | F04B 43/02 |
| | | | | 417/413.3 |
| 2004/0028540 A1 * | 2/2004 | Peck | ...................... | F04B 17/00 |
| | | | | 417/374 |
| 2009/0311117 A1 * | 12/2009 | Gustafsson | ............. | F04B 9/042 |
| | | | | 417/545 |
| 2012/0022456 A1 * | 1/2012 | Salgia | ............... | A61M 5/14224 |
| | | | | 604/181 |
| 2019/0383282 A1 | 12/2019 | Peters et al. | | |
| 2022/0233763 A1 | 7/2022 | Zhang et al. | | |
| 2022/0265917 A1 | 8/2022 | Koh | | |

OTHER PUBLICATIONS

Hurlbatt, Mike, "Characteristics and Best Uses of Diaphragm Pumps", Pump Solutions Australia, Apr. 15, 2016, retrieved from https://pumpsolutions.com.au/characteristics-and-best-uses-of-diaphragm-pumps/.

* cited by examiner

REUSABLE FLUID PUMPING DEVICE

FIELD OF THE INVENTION

The present disclosure generally relates to intravenous sets, and, in particular, to pumping devices for intravenous sets.

BACKGROUND

Medical treatments often include the infusion of a medical fluid (e.g., a saline solution, a liquid medication, or blood) to patients using an intravenous (IV) catheter that is connected though an arrangement of flexible tubing and fittings, commonly referred to as an "IV set," to a source of fluid, for example, an IV bag. During certain operations, devices can be used to pump medical fluid, such as blood, to a patient. In some applications, certain pumps may not provide sufficient flow rates and may cause user fatigue, increasing the complexity and duration of certain surgical procedures.

SUMMARY

The disclosed subject matter relates to pumps for use with IV sets. In certain embodiments, a pump assembly for use with an IV set is disclosed that comprises a rotatable crank comprising a crank profile, the crank profile defining a plurality of lobes; and a piston rod comprising a first follower and a second follower spaced apart from the first follower, wherein the first follower contacts the crank profile to selectively advance the piston rod, the second follower contacts the crank profile to selectively retract the piston rod, and rotation of the crank relative to the piston rod causes the piston rod to reciprocate relative to the crank; and a diaphragm assembly comprising: a housing; and a resilient diaphragm member coupled to the housing and cooperatively defining a volume in fluid communication with the IV set, wherein the diaphragm member is movable between an extended position configured to increase the volume and to draw in fluid from the IV set and a contracted position configured to decrease the volume and to expel fluid into the IV set, and the diaphragm is coupled to the piston rod to reciprocate the diaphragm member between the extended position and the contracted position.

In certain embodiments, a pump assembly for use with an IV set is disclosed that comprises a drive assembly comprising: a drive assembly housing comprising a plurality of tabs; a piston rod comprising an end extending through the drive assembly housing between the plurality of tabs; and a drive mechanism configured to reciprocate the piston rod; and a diaphragm assembly configured to be releasably coupled to the drive assembly, the diaphragm assembly comprising: a diaphragm housing comprising a plurality of windows, wherein the plurality of windows are configured to releasably engage the plurality of tabs of the drive assembly housing; and a resilient diaphragm member coupled to the housing and cooperatively defining a volume in fluid communication with the IV set, wherein the diaphragm member is movable between an extended position configured to increase the volume and to draw in fluid from the IV set and a contracted position configured to decrease the volume and to expel fluid into the IV set, and the diaphragm is releasably coupled to the piston rod to reciprocate the diaphragm member between the extended position and the contracted position.

In certain embodiments, a pump assembly for use with an IV set is disclosed that comprises a rotatable crank comprising a crank profile; a piston rod comprising a first follower and a second follower each in contact with the crank profile, wherein rotation of the crank relative to the piston rod causes the piston rod to reciprocate relative to the crank; a biasing member coupled to the crank and configured to rotate the crank; and a key shaft coupled to the biasing member, wherein the key shaft is rotatable to energize the biasing member; and a diaphragm assembly comprising: a housing; and a resilient diaphragm member coupled to the housing and cooperatively defining a volume in fluid communication with the IV set, wherein the diaphragm member is movable between an extended position configured to draw in fluid from the IV set and a contracted position configured to expel fluid into the IV set, and the diaphragm is coupled to the piston rod to reciprocate the diaphragm member between the extended position and the contracted position.

It is understood that various configurations of the subject technology will become readily apparent to those skilled in the art from the disclosure, wherein various configurations of the subject technology are shown and described by way of illustration. As will be realized, the subject technology is capable of other and different configurations and its several details are capable of modification in various other respects, all without departing from the scope of the subject technology. Accordingly, the summary, drawings and detailed description are to be regarded as illustrative in nature and not as restrictive.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

DETAILED DESCRIPTION

The disclosed pump assembly includes a drive assembly with a rotatable crank that can translate or reciprocate a piston rod, which in turn actuates a diaphragm in fluid communication with a medical fluid. The drive assembly arrangement can allow for high flow rates while allowing for the assembly to be easily actuated by a clinician. Further, the drive assembly can be separated or releasably attached to the diaphragm assembly. Advantageously, by allowing the drive assembly to be removed from the diaphragm assembly, the drive assembly can be reused, while the diaphragm assembly, which comes in contact with medical fluids, can be disposed after use. Further, the drive assembly can be energized by a biasing member. The biasing member allows for the pump assembly to passively pump medical fluid to a patient.

The detailed description set forth below is intended as a description of various configurations of the subject technology and is not intended to represent the only configurations in which the subject technology may be practiced. The detailed description includes specific details for the purpose of providing a thorough understanding of the subject technology. However, it will be apparent to those skilled in the art that the subject technology may be practiced without these specific details. In some instances, well-known structures and components are shown in block diagram form in order to avoid obscuring the concepts of the subject technology. Like components are labeled with identical element numbers for ease of understanding. Reference numbers may have letter suffixes appended to indicate separate instances of a common element while being referred to generically by the same number without a suffix letter.

While the following description is directed to the administration of medical fluid using the disclosed pumping device, it is to be understood that this description is only an example of usage and does not limit the scope of the claims. Various aspects of the pumping device may be used in any application where it is desirable to provide increased fluid flow with reduced user fatigue.

The disclosed pumping assembly overcomes several challenges discovered with respect to certain conventional pumps. One challenge with certain conventional pumps is that certain conventional pumps can have low flow rates and may be difficult to use for extended periods of time. Because certain conventional hand pumps may cause clinicians fatigue during use, the use of certain conventional hand pumps is undesirable.

Therefore, in accordance with the present disclosure, it is advantageous to provide a pumping assembly as described herein that allows for high flow rates and extended use without clinician fatigue.

Examples of pumping assemblies that allow for high flow and extended use are now described.

Figure 1:
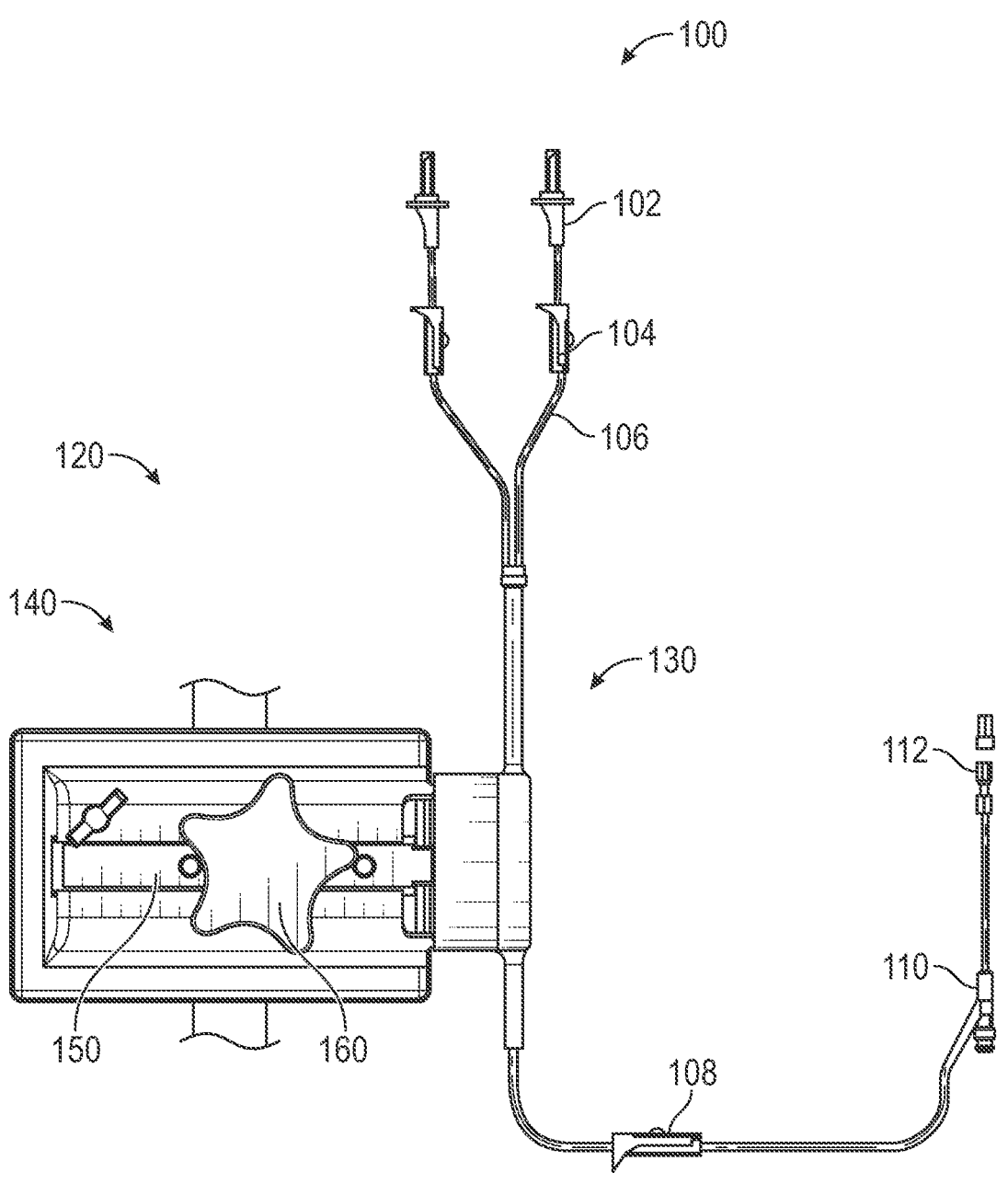
FIG. 1 illustrates an IV set according to certain aspects of the present disclosure.

FIG. 1 illustrates an IV set 100 according to certain aspects of the present disclosure. As described herein, the IV set 100 utilizes a pumping assembly 120 to deliver fluid from a fluid source, such as a container, to a patient through the tubing 106.

In the depicted example, fluid from the fluid source is introduced into the tubing 106 of the IV set 100. As illustrated, the tubing 106 can be terminated with connectors 102 to facilitate coupling and/or fluid communication with the fluid source. In some embodiments, the connectors 102 can be connector spikes that pierce a membrane of the container to permit fluid communication from the container into the tubing 106. Optionally, the tubing 106 can be coupled to the patient via a port 112.

In some applications, additional medical fluids or treatments can be introduced to the patient via the IV set 100. Optionally, additional medical fluids or treatments can be introduced into the IV set 100 via an injection site 110. Further, clamps 104, 108, can control fluid flow through the tubing 106 of the IV set 100.

In the depicted example, the pumping assembly 120 moves, displaces, or otherwise directs medical fluid from a container or other fluid source to the patient via tubing 106. As described herein, the pumping assembly 120 allows for passive pumping of medical fluids with high flow rates and low refill times. Further, portions of the pumping assembly 120, such as the drive assembly 140 can be reused and releasably connected to disposable portions of the pumping assembly 120, such as the diaphragm assembly 130.

Figure 2:
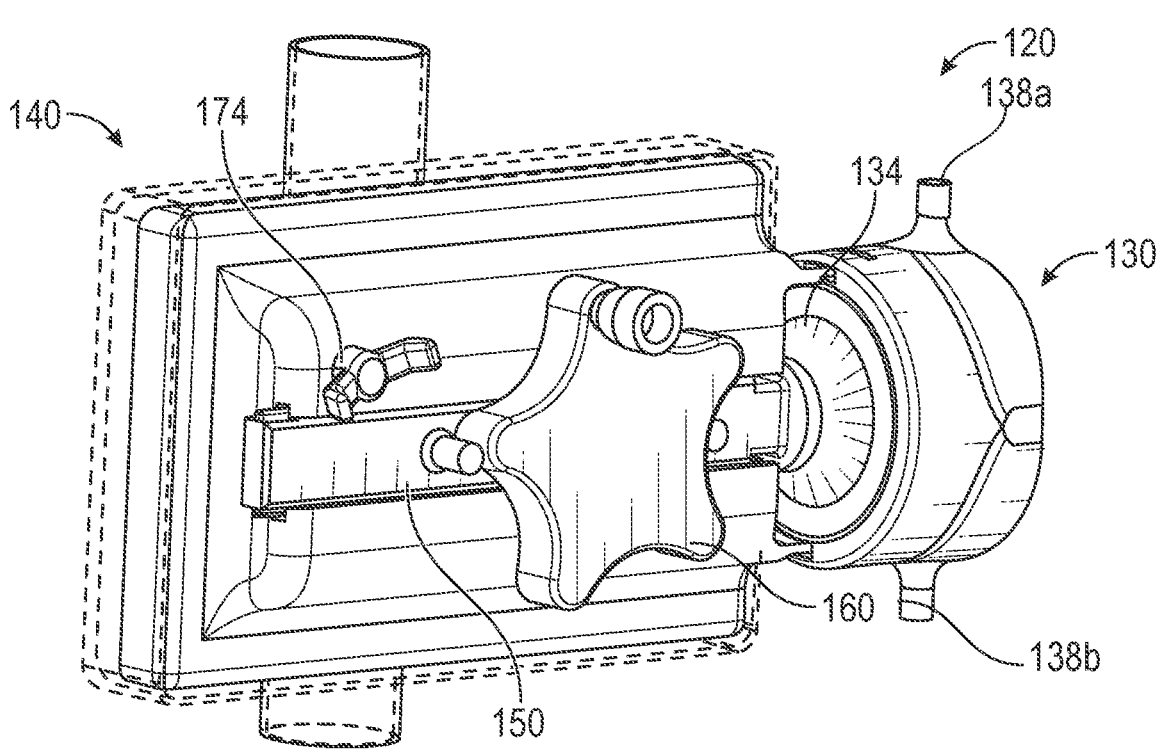
FIG. 2 illustrates the pumping assembly illustrated in FIG. 1.

FIG. 2 illustrates the pumping assembly 120 illustrated in FIG. 1. With reference to FIGS. 1 and 2, the pumping assembly 120 can pump medical fluid, such as blood for transfusions, from tubing 106 connected to a fluid inlet 138a to tubing 106 connected to a fluid outlet 138b. In the depicted example, the pumping assembly 120 includes a drive assembly 140 that actuates a diaphragm assembly 130 to move fluid from the fluid inlet 138a to the fluid outlet 138b.

As illustrated, a piston rod 150 of the drive assembly 140 can reciprocate to move a diaphragm 134 of the diaphragm assembly 130 to cyclically displace or move fluid between the fluid inlet 138a and the fluid outlet 138b. A rotatable crank 160 can engage features of the piston rod 150 to allow rotation of the crank 160 to reciprocally actuate or translate the piston rod 150.

In some embodiments, the crank 160 can be rotated by energized biasing member within the drive assembly 140. A user can wind or introduce energy into the biasing member by rotating or otherwise actuating a key shaft 174. As described herein, the drive assembly 140 can include a gear assembly to provide the user and/or the drive assembly 140 a mechanical advantage.

As described herein, the drive assembly 140 can be fluidly isolated from the medical fluid in the tubing 106 and passing through the fluid inlet 138a and the fluid outlet 138b. As illustrated, the diaphragm assembly 130 is fluidly coupled or in fluid communication with the medical fluid via the fluid inlet 138a and the fluid outlet 138b and isolates the drive assembly 140 from the medical fluid. Advantageously, the drive assembly 140 can be releasably attached or otherwise selectively coupled to the diaphragm assembly 130 to actuate the diaphragm assembly 130. In certain applications, the drive assembly 140 can be used with a diaphragm assembly 130, removed, and reused. In some applications, the diaphragm assembly 130 may be detached from the tubing 106 and disposed after use.

Figure 3:
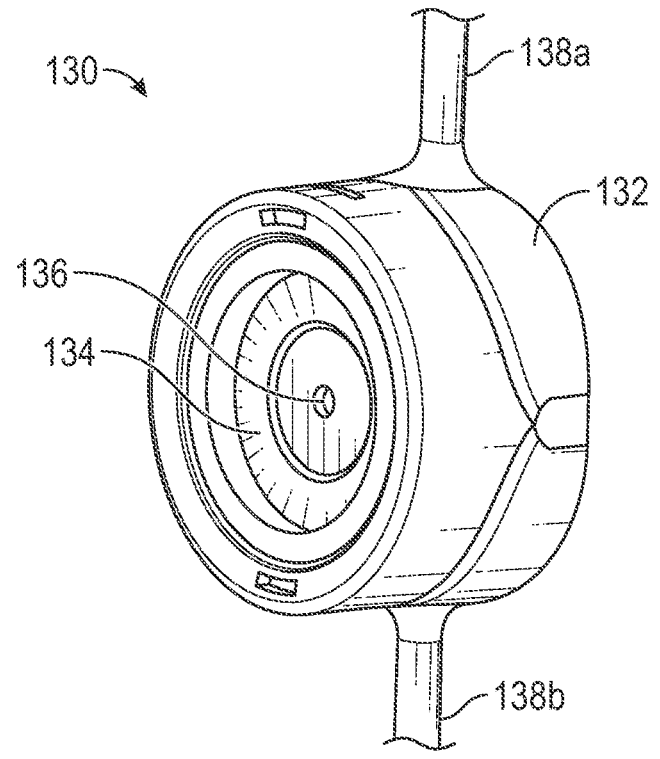
FIG. 3 illustrates a diaphragm assembly of the pumping assembly illustrated in FIG. 1.

FIG. 3 illustrates a diaphragm assembly 130 of the pumping assembly 120 illustrated in FIG. 1. In the depicted example, actuation of the diaphragm assembly 130 moves or displaces medical fluid from the fluid inlet 138a to the fluid outlet 138b. As described herein, the diaphragm assembly 130 can be actuated by a drive assembly 140 releasably attached to the diaphragm assembly 130.

In the depicted example, a diaphragm 134 coupled to a housing 132 defines a volume 133 (illustrated in FIG. 7) that is in fluid communication with the fluid inlet 138a and the fluid outlet 138b. During operation, movement or deflection of the diaphragm 134 can change the size of the volume 133 to draw fluid in or expel fluid out. The diaphragm 134 can be formed from an elastically deformable, resilient, or otherwise suitable material, such as an elastomeric material. In some embodiments, the diaphragm 134 can be overmolded on the housing 132. Further, in some embodiments, the diaphragm 134 can be press fit into the housing 132.

During operation, the diaphragm 134 can be pulled or extended away from the housing 132 to expand the volume 133 of the diaphragm assembly 130, creating a pressure drop, suctioning or drawing in medical fluid from the fluid inlet 138a into the volume 133. In some embodiments, the diaphragm assembly 130 (or other portions of the IV set) can include a one-way valve to prevent the backflow of fluid from the fluid outlet 138*b* during the expansion of the volume 133.

Further, the diaphragm 134 can be contracted or pushed into the housing 132 to contract or reduce the volume 133 of the diaphragm assembly 130 to compress the medical fluid within the volume 133, expelling the medical fluid from the volume 133 into the fluid outlet 138*b* and toward the patient. The diaphragm assembly 130 (or other portions of the IV set) can include another one-way valve to prevent the backflow of fluid from the volume 133 into the fluid inlet 138*a* during the contraction of the volume 133.

During operation, the diaphragm 134 can be deformed or moved manually or by the drive assembly 140. As described herein, the diaphragm 134 can be actuated to be moved or deformed by the piston rod 150 of the drive assembly 140. As described herein, an end of the piston rod 150 can be releasably coupled to a port 136 of the diaphragm 134. The piston rod 150 can engage with a snap feature of the port 136. Further, the diaphragm 134 can serve as a fluid barrier to prevent medical fluid from contacting the drive assembly 140 or the piston rod 150.

In some applications, the cyclical expansion and contraction of the volume 133 caused by the movement of the diaphragm 134 can pump fluid from the fluid inlet 138*a* to the fluid outlet 138*b*. As described herein, the reciprocating motion of the piston rod 150 can actuate the diaphragm 134 in a cyclical fashion to pump fluid to the patient. Advantageously, the arrangement of the pumping assembly 120 allows for increase flow rates and lower refill times compared to certain conventional pumps. For example, embodiments of the pumping assembly 120 can allow flow rates of up to 30 L/min.

Figure 4:
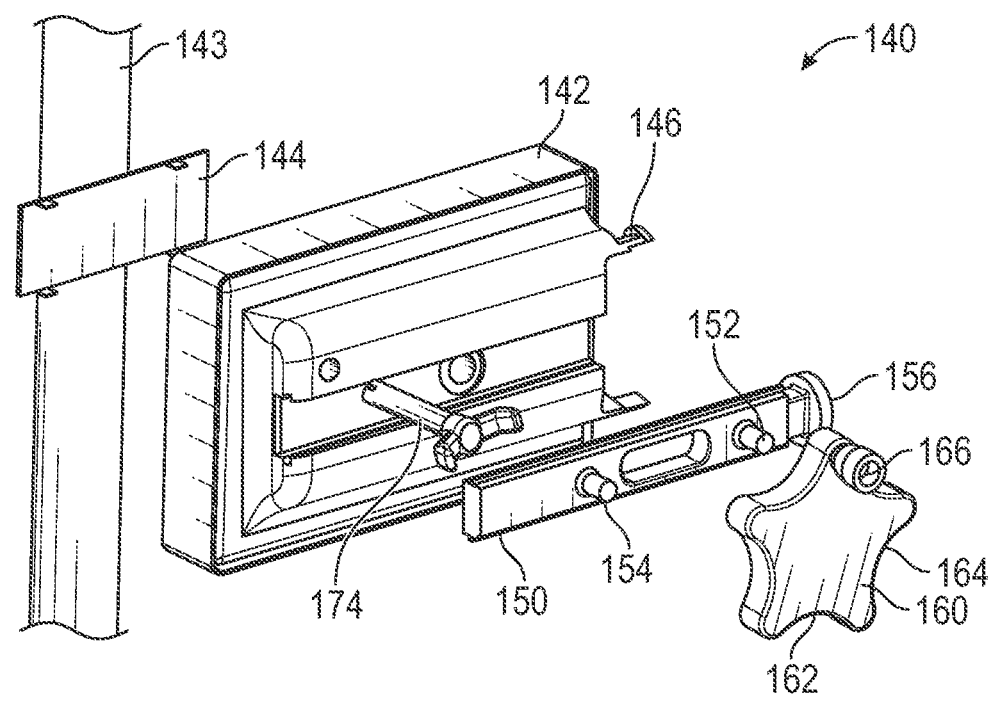
FIG. 4 is an exploded view of the drive assembly of the pumping assembly of FIG. 2.
Figure 5:
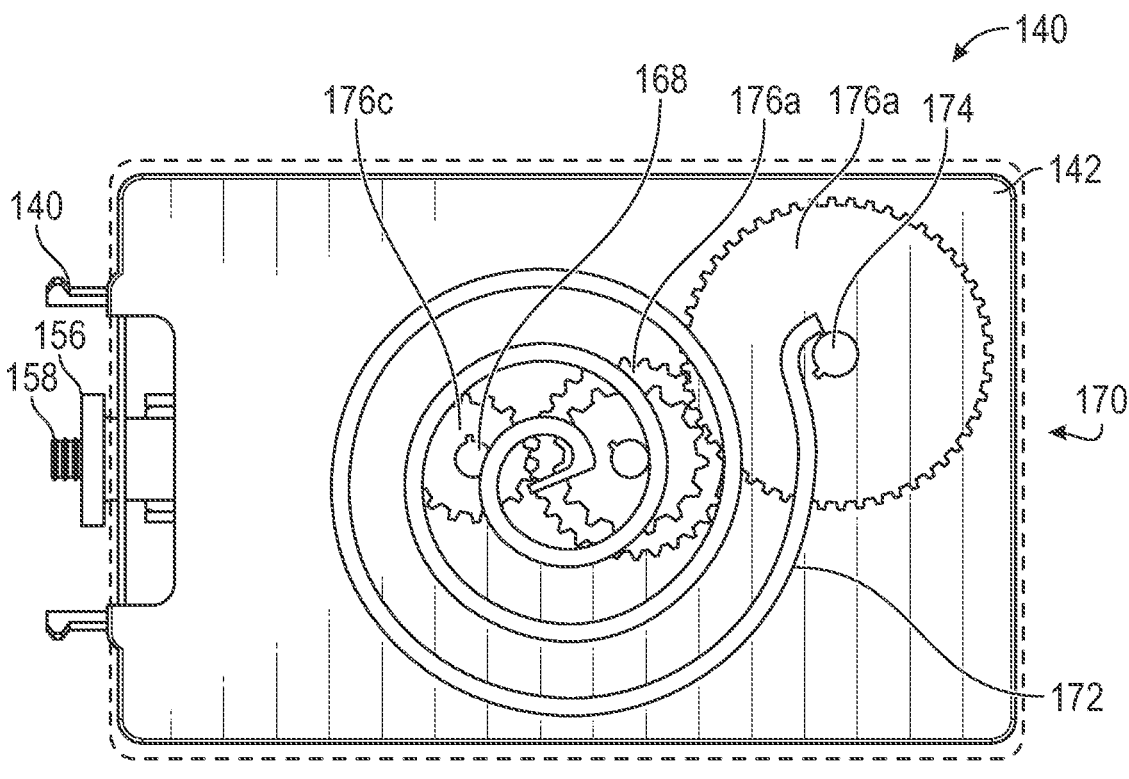
FIG. 5 is partial cross-sectional view of the drive assembly of FIG. 4.

FIG. 4 is an exploded view of the drive assembly 140 of the pumping assembly 120 of FIG. 2. With reference to FIG. 4, the drive assembly 140 reciprocates the piston rod 150 to actuate the diaphragm assembly 130 and pump fluid to the patient. During operation, the piston rod 150 can reciprocate with a desired stroke length and frequency to actuate the diaphragm assembly 130 to provide a desired fluid flow rate. The end 158 of the piston rod 150 (as shown in FIG. 5) can be coupled to the diaphragm 134 via a port 136 defined in the diaphragm 134. A shoulder 156 of the piston rod 150 can abut the diaphragm 134.

In the depicted example, a profile 162 of the crank 160 defines the movement or translation of the piston rod 150. One or more followers 152, 154 coupled to and extending from the piston rod 150 can follow an exterior profile 162 of the crank 160 to translate the piston rod 150 as the crank 160 rotates. The exterior profile 162 of the crank 160 can include one or more curved lobes 164. As illustrated, the exterior profile 162 can have a multi-lobe 164 arrangement. In some embodiments, the exterior profile 162 of the crank 160 can define five lobes 164. The followers 152, 154 can have a generally cylindrical shape to engage or follow the exterior profile 162 of the crank 160, creating a cam and follower arrangement.

During operation, rotation of the crank 160 translates or moves the piston rod 150. As illustrated, a leading follower 152 can engage or follow a leading surface of the exterior profile 162 to advance the piston rod 150 forward toward the diaphragm assembly 130 (toward a compressed or expelling position) based on the geometry of the crank 160. Similarly, a trailing follower 154 can engage or follow a trailing surface of the exterior profile 162 to retract the piston rod 150 away from the diaphragm assembly 130 (toward an extended or suction position) based on the geometry of the crank 160. As illustrated, the leading follower 152 and the trailing follower 154 in conjunction with the exterior profile 162 of the crank 160 can allow the piston rod 150 to reciprocate based on the geometry of the exterior profile of the crank 160. Therefore, the exterior profile 162 of the crank 160 can define the pumping action of the diaphragm assembly 130.

In some embodiments, the crank 160 can be passively rotated by a drive mechanism 170 (described below and shown in FIG. 5) or manually rotated by a clinician via a handle 166. As described below, the drive mechanism 170 can be energized by rotating or winding a key shaft 174. Winding or rotation of the key shaft 174 can energize a spring or biasing member configured to release energy and rotate the crank 160. Advantageously, the arrangement of the drive assembly 140 allows for a clinician to easily actuate the pumping assembly 120, with relatively low force (e.g. 0.2 N-m) and lower fatigue compared to certain conventional pumps.

As illustrated, components of the drive assembly 140 can be disposed within or attached to a housing 142. In some embodiments, the piston rod 150 and the crank 160 are coupled to the housing 142 and portions of the drive mechanism 170 are disposed within the housing 142 internally. Further, as described herein, the housing 142 can include features to releasably attached the drive assembly 140 to the diaphragm assembly 130. For example, the housing 142 can include tabs or fingers 146 disposed around the piston rod 150 that are configured to engage with the diaphragm housing 132 to releasably couple the drive assembly 140 with the diaphragm assembly 130.

In some embodiments, the drive assembly 140 can be coupled to the IV pole 143. As illustrated, the housing 142 can be releasably coupled to a mounting plate 144 that is attached to the IV pole 143. The housing 142 can be attached to the mounting plate 144 with "snap fit" clips or interference fit attachments.

Figures 6, 7:
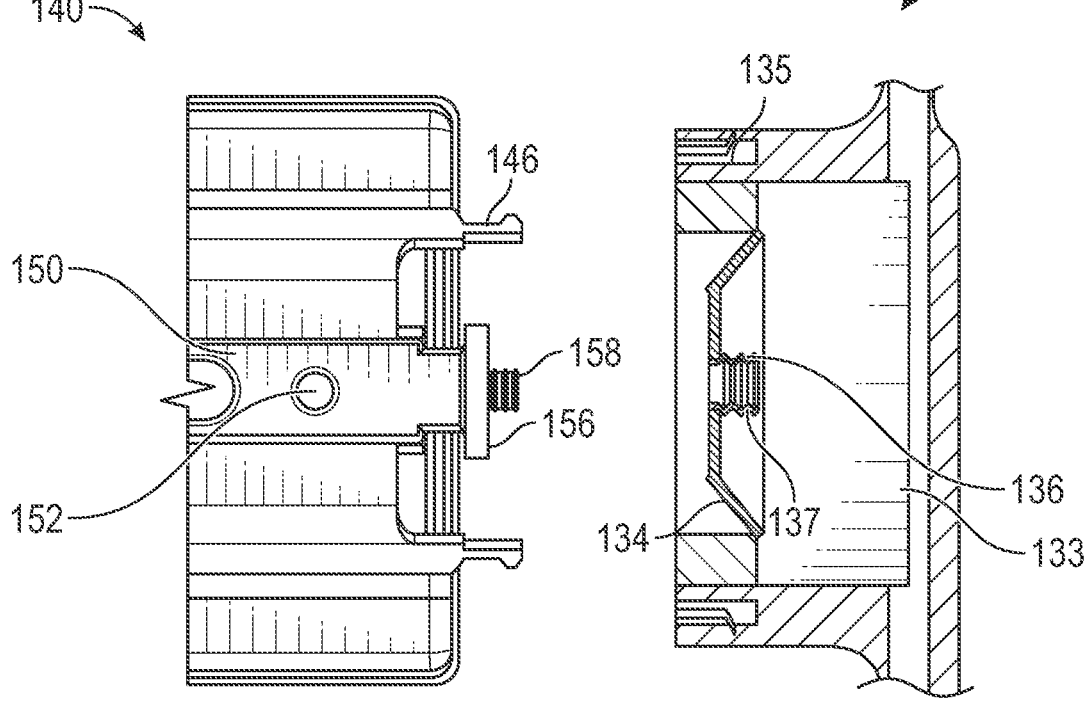
FIG. 6 is a detail view of the drive mechanism of the drive assembly of FIG. 4.
FIG. 7 is a detail view of the drive assembly and the diaphragm assembly interface.

FIG. 5 is partial cross-sectional view of the drive assembly 140 of FIG. 4. FIG. 6 is a detail view of the drive mechanism 170 of the drive assembly 140 of FIG. 4. As described above, in some embodiments, the crank 160 can be rotated by the drive mechanism 170 to allow passive operation of the pumping assembly 120.

In the depicted example, energy to drive the crank 160 can be stored in a biasing member 172. The biasing member 172 can be a spring, such as a torsional spring, or any other suitable device to selectively store and release energy. Energy can be introduced into the biasing member 172 by a user. The user can rotate a key shaft 174 to wind or otherwise energize the biasing member 172. Energy stored in the biasing member 172 can be selectively released to rotate the crank 160.

In some embodiments, the drive mechanism 170 includes one or more intermeshed gears 176*a*, 176*b*, 176*c*. The gears 176*a*, 176*b*, 176*c* can provide a mechanical advantage to the user winding the key shaft 174 to impart energy into the biasing member 172. Further, the gears 176*a*, 176*b*, 176*c* can control the unwinding or release of energy from the biasing member 172 into the crank 160.

Advantageously, the drive mechanism 170 can reduce the amount of fatigue a user experiences compared to certain conventional pumps by reducing the amount of prolonged manual input required to operate the pumping assembly 120. In some applications, the drive mechanism 170 can provide sufficient energy for 20 actuations of the diaphragm assembly 130 (i. e. displacing approximately 152 mL). In some embodiments, the drive mechanism 170 can reduce the amount of torque required (0.2 N-m) to actuate the pumping assembly 120 compared to certain conventional pumps. Further, in some embodiments, the pumping assembly 120 can allow for a passive flow rate that is significantly higher that certain conventional pumps (e.g. 515 mL/min compared to 300 mL/min).

Figures 8, 9:
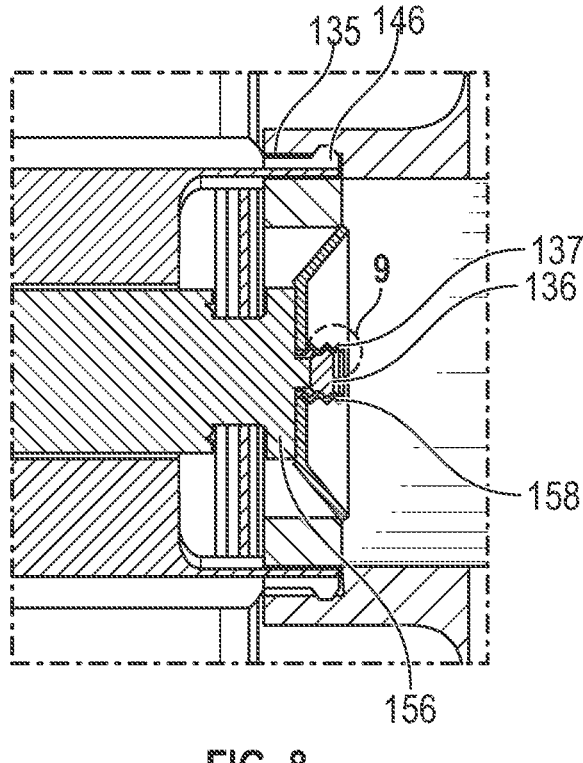
FIG. 8 is a detail view of the drive assembly and the diaphragm assembly attached.
FIG. 9 is a detail view of the piston rod of the drive assembly and the diaphragm of the diaphragm assembly.

FIG. 7 is a detail view of the drive assembly 140 and the diaphragm assembly 130 interface. FIG. 8 is a detail view of the drive assembly 140 and the diaphragm assembly 130 attached. As described herein, the drive assembly 140 and the diaphragm assembly 130 can include features to allow these components to be releasably attached. Advantageously, since the drive assembly 140 is fluidly isolated from the medical fluid, the drive assembly 140 can be removed from the diaphragm assembly 130 after use, allowing for the drive assembly 140 to be reused and the diaphragm assembly 140 to be disposed.

As illustrated, resilient fingers 146 extending from the housing 142 of the drive assembly 140 can engage with windows 135 defined in the diaphragm housing 132 of the diaphragm assembly 130. The windows 135 can be disposed circumferentially around the diaphragm 134. The resilient fingers 146 can be biased outward to engage the edges of the windows 135 to couple the drive assembly 140 with the diaphragm assembly 130. The drive assembly 140 can be released from the diaphragm assembly 130 by depressing the fingers 146 inward.

FIG. 9 is a detail view of the piston rod 150 of the drive assembly 140 and the diaphragm 134 of the diaphragm assembly 130. With reference to FIGS. 7-9, in addition to the releasable attachment of the housings 132, 142 of the diaphragm assembly 130 and the drive assembly 140, respectively, the piston rod 150 can be releasably attached to the diaphragm 134. As illustrated, grooves 159 of the piston rod end 158 can engage with features 137 of the port 136 of the diaphragm 134 to releasably couple the piston rod 150 with the diaphragm 134. In some embodiments, the piston rod end 158 can have an annular "snap fit" or interference fit with the port 136 of the diaphragm 134 to allow the piston rod 150 to actuate the diaphragm 134. As illustrated, the shoulder 156 of the piston rod 150 can abut against a portion of the diaphragm 134. In some embodiments, the angle of contact between the grooves 159 of the piston rod 150 and the features 137 of the port 136 can be adjusted to allow for a desired retention force. Advantageously, the retention force between the grooves 159 and the features 137 can be configured based on the actuation force of the piston rod 150 relative to the diaphragm 134 to prevent inadvertent release of the piston rod 150 from the diaphragm 134 during operation while permitting intentional release by a user.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

In one aspect, the term "coupled" or the like may refer to being directly coupled. In another aspect, the term "coupled" or the like may refer to being indirectly coupled.

Terms such as "top," "bottom," "front," "rear" and the like if used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Various items may be arranged differently (e.g., arranged in a different order, or partitioned in a different way) all without departing from the scope of the subject technology. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but is to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A pump assembly for use with an IV set, the pump assembly comprising:

a rotatable crank with an exterior profile that defines a plurality of lobes;

a biasing member coupled to the crank and configured to rotate the crank;

a piston rod comprising a first follower and a second follower spaced apart from the first follower, wherein the first follower contacts the exterior profile to selectively advance the piston rod, the second follower contacts the exterior profile to selectively retract the piston rod, and rotation of the crank in a single rotation direction relative to the piston rod causes the piston rod to cyclically reciprocate relative to the crank; and a diaphragm assembly comprising:

a housing; and a resilient diaphragm member coupled to the housing and cooperatively defining a volume in fluid communication with the IV set, wherein the diaphragm member is movable between an extended position configured to increase the volume and to draw in fluid from the IV set and a contracted position configured to decrease the volume and to expel fluid into the IV set, and the diaphragm member is coupled to the piston rod to reciprocate the diaphragm member between the extended position and the contracted position.

2. The pump assembly of claim 1, further comprising a key shaft coupled to the biasing member, wherein the key shaft is rotatable to energize the biasing member.

3. The pump assembly of claim 1, comprising a plurality of gears coupled to the biasing member and the crank.

4. The pump assembly of claim 1, wherein the crank is manually rotatable.

5. The pump assembly of claim 1, wherein the diaphragm member is releasably coupled to the piston rod.

6. The pump assembly of claim 1, further comprising a check valve in fluid communication with the volume to prevent backflow of fluid into the volume.

7. The pump assembly of claim 1, wherein the plurality of lobes are each spaced apart along an entirety of the exterior profile about an axis of rotation.

8. The pump assembly of claim 1, wherein the biasing member comprises a torsional spring.

9. A pump assembly for use with an IV set, the pump assembly comprising:

a rotatable crank;

a piston rod comprising a first follower and a second follower each in contact with an exterior profile of the crank, wherein rotation of the crank in a single rotation direction relative to the piston rod causes the piston rod to cyclically reciprocate relative to the crank;

a biasing member coupled to the crank and configured to receive energy and rotate the crank upon release of the energy; and a key shaft coupled to the biasing member, wherein the key shaft is rotatable to provide energy to the biasing member; and a diaphragm assembly comprising:

a housing; and a resilient diaphragm member coupled to the housing and cooperatively defining a volume in fluid communication with the IV set, wherein the diaphragm member is movable between an extended position configured to draw in fluid from the IV set and a contracted position configured to expel fluid into the IV set, and the diaphragm is coupled to the piston rod to reciprocate the diaphragm member between the extended position and the contracted position.

10. The pump assembly of claim 9, comprising a plurality of gears coupled to the biasing member and the crank.

11. The pump assembly of claim 9, wherein the crank is manually rotatable.

12. The pump assembly of claim 9, wherein the diaphragm member is releasably coupled to the piston rod.

13. The pump assembly of claim 9, further comprising a check valve in fluid communication with the volume to prevent backflow of fluid into the volume.

14. The pump assembly of claim 9, wherein the biasing member comprises a torsional spring.

* * * * *